United States Patent
Li et al.

(10) Patent No.: US 11,376,216 B2
(45) Date of Patent: Jul. 5, 2022

(54) PERIODONTAL DISEASE THERAPY

(71) Applicant: New York University, New York, NY (US)

(72) Inventors: Xin Li, New York, NY (US); Deepak Saxena, New York, NY (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 16/959,614

(22) PCT Filed: Dec. 31, 2018

(86) PCT No.: PCT/US2018/068161
§ 371 (c)(1),
(2) Date: Jul. 1, 2020

(87) PCT Pub. No.: WO2019/136022
PCT Pub. Date: Jul. 11, 2019

(65) Prior Publication Data
US 2020/0383902 A1   Dec. 10, 2020

Related U.S. Application Data

(60) Provisional application No. 62/612,850, filed on Jan. 2, 2018.

(51) Int. Cl.
*A61K 9/00* (2006.01)
*A61P 1/02* (2006.01)
*A61K 31/4375* (2006.01)
*A61K 47/36* (2006.01)

(52) U.S. Cl.
CPC .......... *A61K 9/006* (2013.01); *A61K 31/4375* (2013.01); *A61K 47/36* (2013.01); *A61P 1/02* (2018.01)

(58) Field of Classification Search
CPC .... A61K 9/006; A61K 31/4375; A61K 47/36; A61P 1/02
See application file for complete search history.

(56) References Cited

U.S. PATENT DOCUMENTS 5,447,940 A    9/1995 Harvey et al.
8,975,275 B2   3/2015 Schulz et al.

FOREIGN PATENT DOCUMENTS

WO    2017/142855 A1    8/2017

OTHER PUBLICATIONS

PUBCHEM-CID: 53358775, create date Sep. 19, 2011, pp. 1-14.
Guo, Y., et al., Succinate and its G-protein-coupled receptor stimulates osteoclastogenesis, Nature Communications, May 2017, vol. 8, 15621, pp. 1-12.
Li et al., Metformin Improves Diabetic Bone Health by Re-Balancing Catabolism and Nitrogen Disposal, PLoS ONE 10 (12): e0146152.
Guo et al., Succinate and its G-protein-coupled receptor stimulates osteoclastogenesis. Nat. Commun. 8, 15621 (2017).
Bhuniya et al., Discovery of a potent and selective small molecule hGPR91 antagonist, Bioorg. & Med. Chem. Lett. 21(12)3596-3602(2011).

*Primary Examiner* — Robert A Wax
*Assistant Examiner* — Olga V. Tcherkasskaya
(74) *Attorney, Agent, or Firm* — Hodgson Russ LLP

(57) ABSTRACT

Disclosed are formulations for oral films and other compositions containing therapeutic agents. The therapeutic agents interfere with succinate/succinate receptor signaling. The films and compositions of the present disclosure can be used to treat periodontal disease.

16 Claims, 9 Drawing Sheets

PERIODONTAL DISEASE THERAPY

CROSS REFERENCE TO RELATED APPLICATION

This application claims priority to U.S. Provisional Application No. 62/612,850, filed on Jan. 2, 2018, the disclosure of which is incorporated by reference.

FIELD OF THE DISCLOSURE

The present disclosure relates to oral compositions and formulations for treating periodontal disease.

BACKGROUND OF THE DISCLOSURE

Periodontitis is a common chronic inflammatory disease characterized by destruction of the supporting structures of the teeth (the periodontal ligament and alveolar bone). It is highly prevalent (severe periodontitis affects 10-15% of adults) and has multiple negative impacts on quality of life. Epidemiological data confirm that diabetes is a major risk factor for periodontitis; susceptibility to periodontitis is approximately fivefold higher in people with diabetes. According to the International Diabetes Federation, the number of people with diabetes rose from 108 million in 1980 to 422 million in 2014 and it is estimated that by 2040 this number will increase to 642 million. In the USA alone 29.1 million people (9.3% of the U.S. population) have diabetes. Type 2 diabetes (T2D), constitutes approximately 85 to 90 percent of all cases, and results from insulin resistance rather than from the total absence of insulin production. The chronic inflammatory condition of periodontitis is induced by pathogenic biofilms or dental plaque, which accumulates on the tooth surface. Microbial analysis of affected periodontal sites indicated the presence of a complex microflora mainly consisting of spirochetes and gram negative anaerobes. T2D is considered to alter the bacterial composition of subgingival plaque. It has been reported that periodontal pathogens exhibit metabolic symbioses. The metabolites are altered in T2D that may dysregulate oral homeostasis to increase inflammation and bone loss. Succinate is a significantly elevated metabolite in T2D mice and patients. However, the role of succinate and succinate receptor 1 (Sucnr1) signaling has not been evaluated in periodontal disease.

Periodontal disease also affects non-human animals. For example, periodontal disease is considered to affect over 87% of dogs and 70% of cats over three years of age. If left untreated, periodontal disease may cause multiple problems in the oral cavity and may even lead to damage to internal organs in some pets as they age.

As such, there is a continuing need for development of agents that can be used to treat periodontal disease in both humans and animals.

SUMMARY OF THE DISCLOSURE

The present disclosure provides oral compositions including oral films, and methods for treatment of periodontal disease using the oral compositions or films.

In an aspect, the present disclose provides oral formulations and oral films comprising therapeutic agents targeted to interfering with succinate/succinate receptor signaling. For example, the present disclosure provides oral films and oral formulations comprising one or more compounds having the following formula:

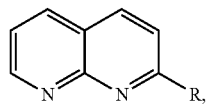

Structure I where R selected from the group consisting of a hydrogen atom, an alkyl group (e.g., methyl, ethyl, propyl, isopropyl, and the like), a COOR' group, where R' is an alkyl group (e.g., methyl, ethyl, propyl, isopropyl, and the like), or

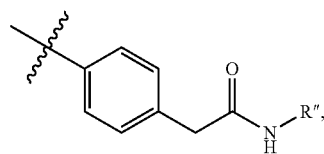

where R" is selected from the group consisting of a hydrogen atom, an alkyl group (e.g., methyl, ethyl, propyl, isopropyl, and the like), and

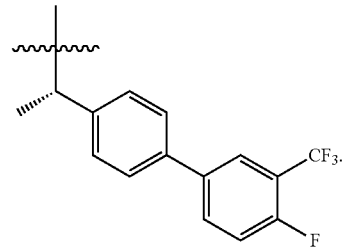 [SMILES: *[C@@H](C)c1ccc(-c2ccc(F)c(C(F)(F)F)c2)cc1]

The compounds may be present as succinate salts.

In an embodiment, the compound in the oral formulations or oral films has the following structure:

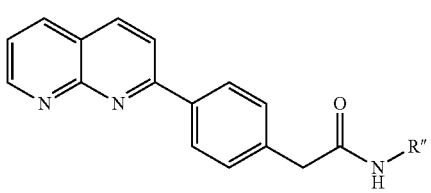

where R" is selected from the group consisting of a hydrogen atom, an alkyl group (e.g., methyl, ethyl, propyl, isopropyl, and the like), and

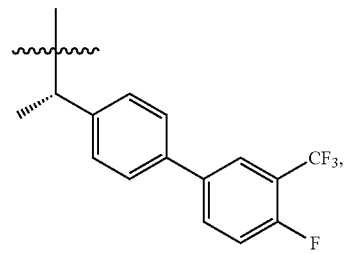 [SMILES: *[C@@H](C)c1ccc(-c2ccc(F)c(C(F)(F)F)c2)cc1]

and where Z is optional and when present, is a succinate group.

In an aspect, this disclosure provides a method of treatment of periodontal disease comprising exposing the gums to oral compositions or oral films comprising an inhibitor of succinate/succinate receptor pathway. An example of an inhibitor is an agent that interferes with the binding of succinate to its receptor. Examples of inhibitor of succinate/succinate receptor pathway include compounds of Structure I, Structure II or succinate salts thereof. A specific example is compound 4C (Structure III). Substitutions and variants of this structure which have the same or similar activity on the succinate/Sucnr1 are also included, such as, for example, compounds 7a and 7b (FIG. 7). The formulations can be used in the form of oral films or other oral formulations.

The oral compositions and oral films can be used for prevention and treatment of periodontal disease for humans as well as for veterinary use.

DESCRIPTION OF THE DRAWINGS

For a fuller understanding of the nature and objects of the disclosure, reference should be made to the following detailed description taken in conjunction with the accompanying figures.

DETAILED DESCRIPTION OF THE DISCLOSURE

Figure 1:
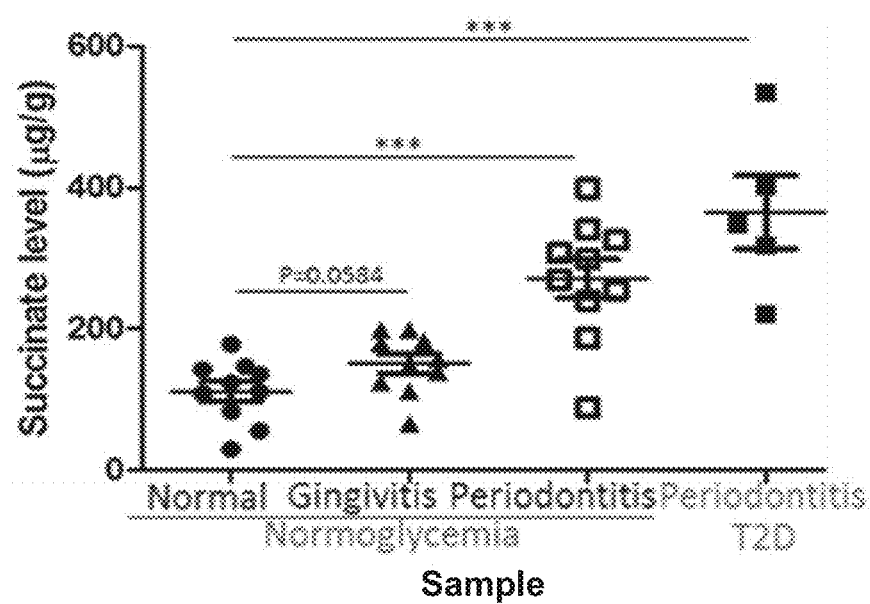
FIG. 1 shows gingival crevicular fluid (GCF) succinate levels. GCF was collected using Whatman filter paper strip and weighted. The samples were dissolved with deionized water, mixed and centrifuged and succinate concentrations in the supernatants were measured using Succinate Colorimetric kit. The succinate levels in GCF were calculated based on the initial sample weight. T2D: Un-controlled diabetes.

The present disclose provides oral films and other oral formulations comprising therapeutic agents targeted to interfering with succinate/succinate receptor signaling. These films and formulations can be used for treatment or prevention of periodontal disease. In an embodiment, the present oral films and formulations can be used by individuals afflicted with diabetes, including type 2 diabetes. The oral films and formulations can also be used for veterinary applications.

Whenever a singular term is used in this disclosure, a plural term is also included. For example, "a", or "an" also includes a plurality of the referenced items, unless otherwise indicated.

The term "therapeutically effective amount" as used herein refers to an amount of an agent sufficient to achieve, in a single or multiple doses, the intended purpose of treatment. Treatment does not have to lead to complete cure, although it may. Treatment can mean alleviation of one or more of the symptoms or markers of the indication. The exact amount desired or required will vary depending on the composition used, its mode of administration, patient specifics and the like. Appropriate effective amount can be determined by one of ordinary skill in the art informed by the instant disclosure using only routine experimentation. Treatment can be orientated symptomatically, for example, to suppress symptoms. It can be effected over a short period, over a medium term, or can be a long-term treatment, such as, for example within the context of a maintenance therapy. Treatment can be continuous or intermittent.

Where a range of values is provided in this disclosure, it should be understood that each intervening value, to the tenth of the unit of the lower limit between the upper and lower limit of that range, and any other intervening value in that stated range is encompassed within the invention, unless clearly indicated otherwise. The upper and lower limits of these smaller ranges may independently be included in the smaller ranges encompassed within the disclosure.

It is considered that the oral compositions of the present disclosure can act to suppress succinate/Sucnr1 activation thereby reducing inflammation and/or periodontal bone loss. The present findings have revealed a role of succinate in regulating oral microenvironment and periodontal bone loss. It was found that (1) the gastrointestinal microbiome was significantly altered in high-fat-diet (HFD) induced T2D mice compared to wild type (WT), (2) succinate favors the growth of periodontal pathogens in vitro; and (3) succinate increases inflammatory factor expression, osteoclastogenesis, and bone resorption in vivo. (4) Sucnr1 antagonist inhibits succinate-stimulated osteoclastogenesis in vitro and in vivo with as little as two days of treatment. (5) Succinate failed to stimulate osteoclastogenesis in the absence of Sucnr1 in vitro. (6) SUCNR1 knock-out mice are protected from periodontal bone loss.

Based on one or more of the findings described herein, in one aspect, this disclosure provides oral film strips and other oral formulations comprising an inhibitor of the succinate/Sucnr1 pathway. In an aspect, the present disclosure provides oral formulations and oral films comprising therapeutic agents targeted to interfering with succinate/succinate receptor signaling. For example, the present disclosure provides oral films and oral formulations comprising compounds having the following formula:

Structure I

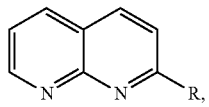

where R selected from the group consisting of a hydrogen atom, an alkyl group (e.g., methyl, ethyl, propyl, isopropyl, and the like), a COOR' group, where R' is an alkyl group (e.g., methyl, ethyl, propyl, isopropyl, and the like), or

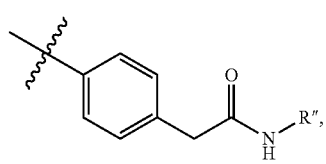

where R" is selected from the group consisting of a hydrogen atom, an alkyl group (e.g., methyl, ethyl, propyl, isopropyl, and the like), and

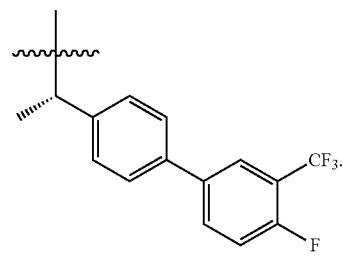 [SMILES: *[C@@H](C)c1ccc(-c2ccc(F)c(C(F)(F)F)c2)cc1]

In an embodiment, the agent interfering with succinate/succinate receptor signaling is a succinate salt of Structure I and may be represented as follows:

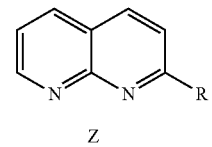

Wherein Z is a succinate group.

In an embodiment, the compound interfering with succinate/succinate receptor signaling has the following structure:

Structure II

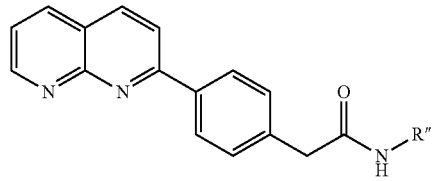

where R" is selected from the group consisting of a hydrogen atom, an alkyl group (e.g., methyl, ethyl, propyl, isopropyl, and the like), and

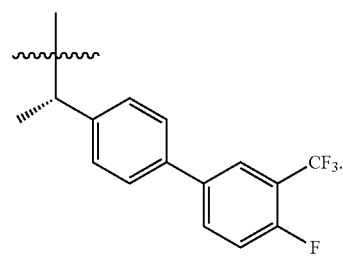 [SMILES: *[C@@H](C)c1ccc(-c2ccc(F)c(C(F)(F)F)c2)cc1]

In an embodiment, the agent interfering with succinate/succinate receptor signaling is a succinate salt of Structure II and may be represented as follows:

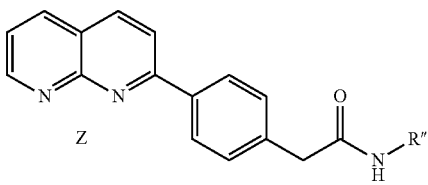

where Z is a succinate group.

In one embodiment, this disclosure provides oral films and oral film formulations comprising one or more compounds of Formula I or II. In an embodiment, the compound is 4C, an antagonist of Sucnr1. Data is presented here in an animal model to show that the oral strips protected the animals from periodontal bone loss.

The structure of 4C is shown below. It can be obtained commercially and is also described in Bhuniya et al. (Bioorganic and Medicinal Chemistry Letters, 21 (2011), 3596-3602), wherein the compound is referred to as 4C, and the disclosure of which, relative to the compound 4C, is incorporated herein by reference.

Structure III

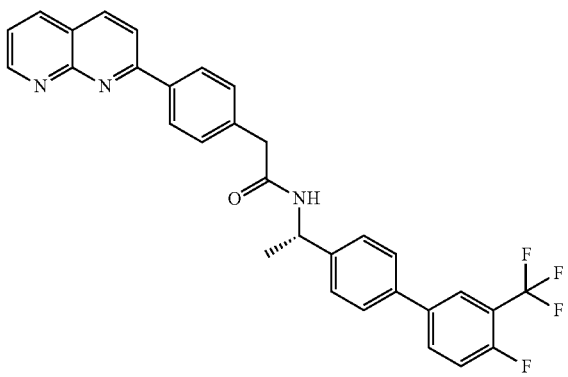

In an embodiment, the agent interfering with succinate/succinate receptor signaling is a succinate salt of Structure III and may be represented as follows:

Structure IV

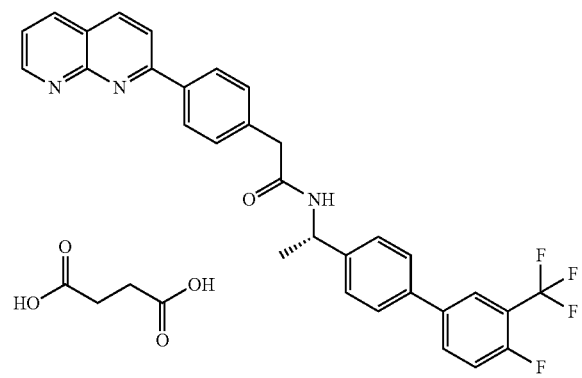

Figure 6:
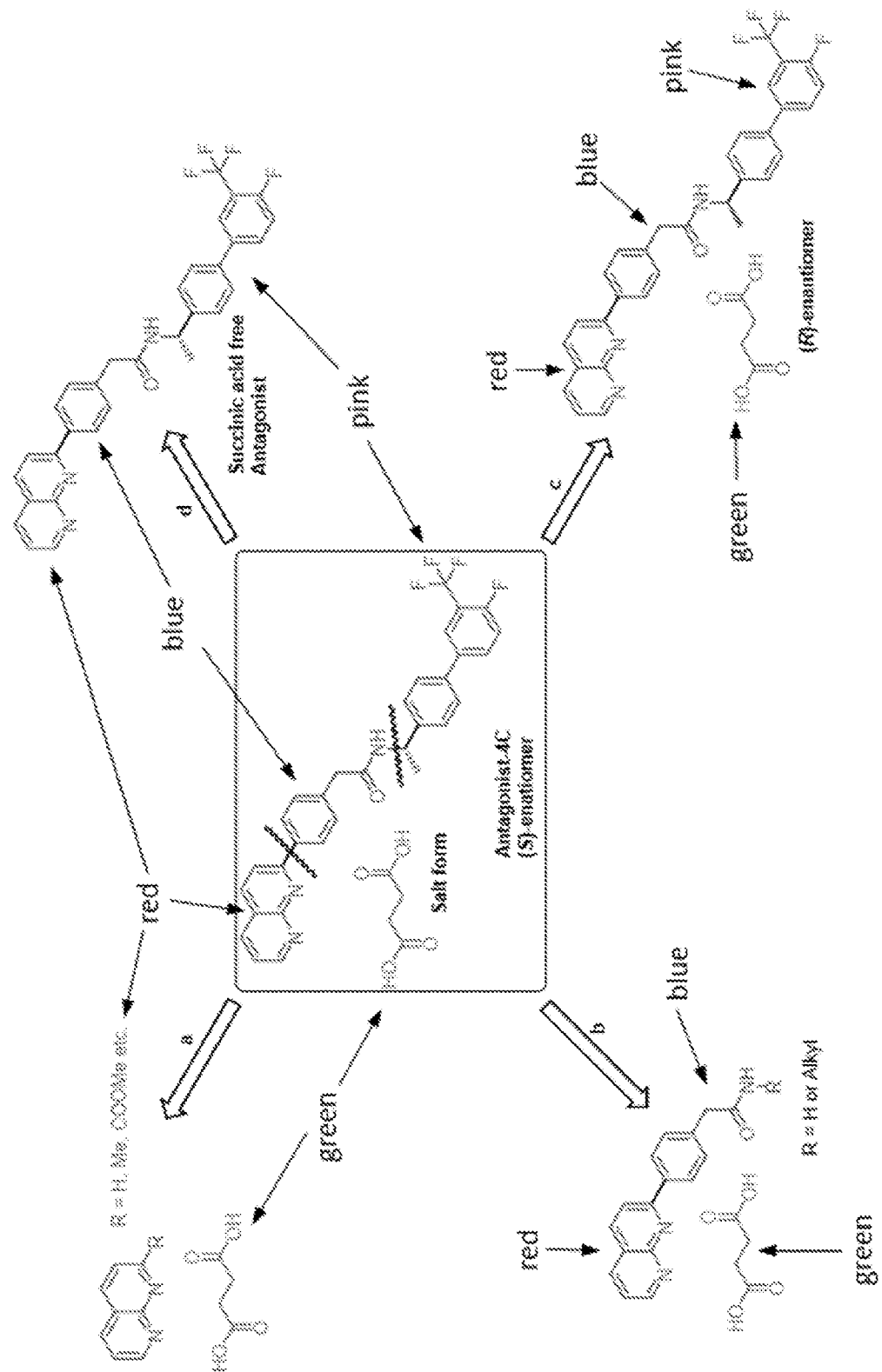
FIG. 6 shows the structure of antagonist 4C and other compounds of the present disclosure.

The antagonist-4C is broadly a hybrid structure of four components, i) 1,8-Naphthyridine moiety (in red, FIG. 6), ii) amide linker (in blue, FIG. 6), iii) biaryl moiety (in pink, FIG. 6), iv) Succinic acid (in green, FIG. 6). In some embodiments, the present disclosure provides 4C analogs, where the 1,8-naphthyridine moiety is kept intact. For example, one or more of the 4C analogs comprise derivatives of the amide linker, biaryl moiety and succinic acid. Various examples include those that change antagonist structure minimally without compromising the biological properties, (such as in, FIGS. 6a & b), and chiral variants (FIG. 6c), and succinic acid salt form (FIG. 6 d).

In an embodiment, the disclosure provides oral films and oral film formulations comprising compounds 7a (may be referred to herein as cpd 7a or cpd-7a) and or 7b (may be referred to herein as cpd7a or cpd-7b).

cpd-7a

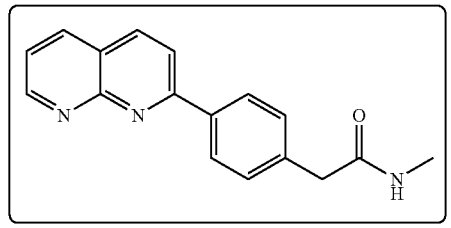

cpd-7b

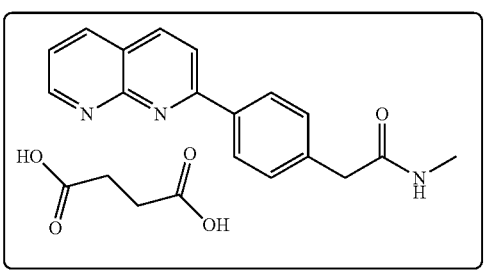

Figure 7:
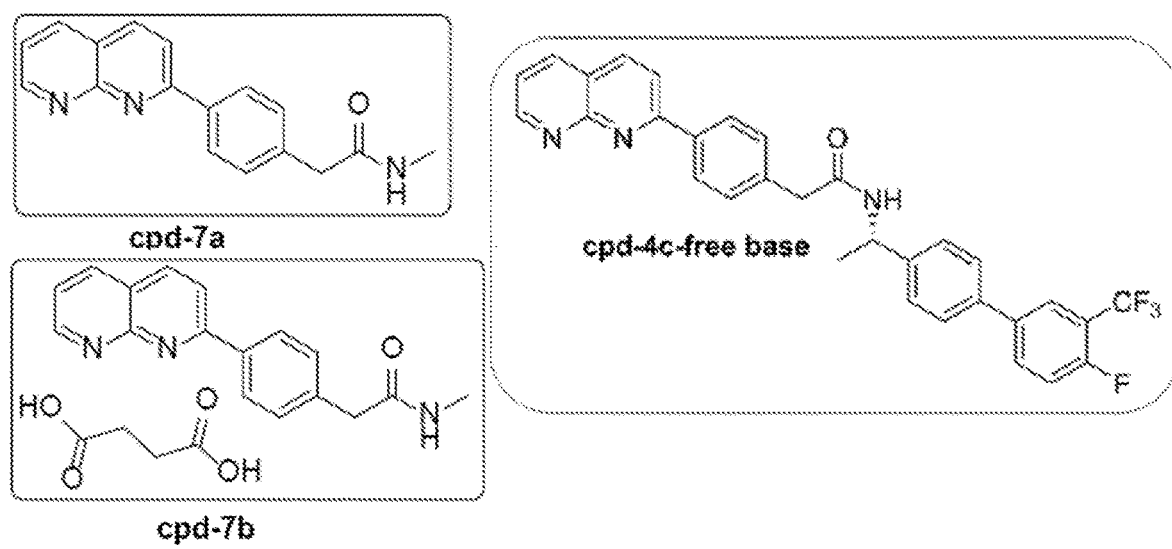
FIG. 7 shows the structure of compounds 7a, 7b, and 4c free base.

In an embodiment, the oral compositions or oral films may comprise one or more of compounds 4C (or succinate salt thereof), 7a and 7b (FIG. 7).

In as aspect, this disclosure provides compounds having the structure of 7a and 7b, and compositions comprising compounds 7a and 7b. The compositions may comprise carriers, such as pharmaceutical carriers.

In an embodiment, the only compounds interfering with succinate/succinate receptor signaling are the compounds of Structure I, Structure II, Structure III, 4C, 7a, and/or 7b. In an embodiment, the compounds interfering with succinate/succinate receptor signaling (such as compounds of Structure I, Structure II, Structure II, Structure III, succinate salts thereof, 4C, succinate salt thereof, 7a, and/or 7b) are used in the present formulations/films at very high purity, such as being at least 80%, 85%, 90%, 95%, 96%, 97%, 98%, 99% or 100% pure—as verified by analytical methods, such as HPLC).

In one aspect, this disclosure provides a method of treatment of periodontal disease comprising exposing the gums to oral compositions or oral films comprising or consisting essentially of, one or more inhibitors of succinate/succinate receptor pathway, such as one or more compounds of the Formula I, II or III, or succinate salts thereof. An example of an inhibitor is an agent that interferes with the binding of succinate to its receptor. For example, the oral compositions or oral films may comprise one or more of 4C, succinate salt thereof, 7a and 7b (FIG. 7).

The present oral films and formulations provide less invasive, cost-effective and practical treatment alternative to the traditional management strategies for periodontal disease, which can be a multistep process (e.g., scaling and root planning, deep cleaning of the teeth, systemic subantimicrobial-dose doxycycline, systemic antimicrobials and lasers) and which can be painful and invasive, particularly in patients with impaired wound healing such as diabetic population. The present compositions and methods can be particular useful in individuals with periodontal disease who are also afflicted with diabetes, such as type 2 diabetes.

In an example, an individual can be a human or a non-human subject. Non-limiting examples of non-human subjects includes domestic animals (e.g., dogs, cats, and the like), farm animals (e.g., horses, pigs, and the like), dairy animals (e.g., cows and the like), and the like.

The present formulations can be controlled and sustained drug release formulations for periodontal disease including dental gels, in situ gels, strips/films etc. The formulations can comprise biodegradable polymers, which may be natural or synthetic. For example, the polymers may be one or more of chitosan, gellan gum, pectin (natural polymers) and Carbopol 974P, Hydroxy propyl methyl cellulose (HPMC), Poloxamers, methyl cellulose (synthetic/semi-synthetic gelling polymers). The films can be prepared by standard methods, such as casting or dispersion, etc. The polymer may be an alginate, such as, for example, calcium alginate.

The oral film formulations comprise a succinate antagonist. In an embodiment, the formulations can be in the form of nanoparticles incorporated into a biopolymer that can undergo biodegradation. This can be formed as a film and/or gel that can be inserted as a strip into the gingival or periodontal pocket or applied on to gingiva. Films that conform to the size and shape of the pockets can be formed to enhance contact between antagonist and gingival tissue thereby increasing treatment effectiveness as well as maximizing patient comfort.

The amount of the antagonist (also referred to herein as the inhibitor) and the vehicle (e.g., polymer) can be varied to provide desired activity, release, and other characteristics. For example, the antagonist to polymer ratio (w/w) can be 0.01:100 to 1:100. In an example, the antagonist to polymer ratio is 1:50. In one example, polymers, such as gelatin, chitosan or cellulose based biodegradable polymer vehicles are present at from 4-16% concentration.

In one embodiment, the thickness of the oral films can range from 0.05 to 0.4 mm, including all 0.01 mm values and ranges therebetween. For example, the thickness can be from 0.07-0.350 mm.

The concentration of therapeutic agent can be from 1-200 µM, including all 0.1 µM values and ranges therebetween. In embodiments, the concentration of the antagonist is 5 µM, 10 µM, 20 µM, 50 µM, 100 µM, 150 µM or 160 µM.

The present formulations can be used for treatment of gum disease. Some non-limiting examples of use of the present formulations are as follows. In an embodiment, treatment is based on the stage of gum disease. Gingivitis is the earliest stage of gum disease, an inflammation of the gums caused by plaque buildup at the gum line. Bacteria produce toxins that can irritate the gum tissue, causing gingivitis. There can be some bleeding during brushing and flossing. The bone and connective tissue that hold the teeth in place are generally not yet affected. At this early stage in gum disease, the present agents may be used as a gel/toothpaste based formulation which can be applied by an individual without the need of a dentist.

Periodontitis is a stage where the supporting bone and fibers that hold the teeth in place are irreversibly damaged. Gums may begin to form a pocket below the gum line, which traps food and plaque. At this stage, the present formulations can be used as oral films which can be inserted in the gum pocket by dentist. The films are biodegradable and generally degrade within 2-3 days, after which new films can be applied. Individuals may also continue using gel/toothpaste at home.

Advanced Periodontitis is a stage which is a chronic stage of gum disease, the fibers and bone supporting teeth are destroyed, which can cause teeth to shift or loosen. This can affect bite and, if aggressive treatment is not able to salvage the structures, teeth may need to be removed. At this chronic stage, the present formulations can be used as oral strips, such as, as prescribed by a dentist. The individuals may still also continue to use gel/toothpaste at home.

In an embodiment, the compounds (also referred to herein as antagonists), such as 4C, succinate salt thereof, 7a and 7b, that can target succinate receptor and block succinate signaling in gingival tissue, can be used in particular form. The particles can be incorporated into a polymer (e.g., biopolymer) to form a composite film that can be inserted as a strip into the gingival or periodontal pocket. After insertion, the composite will biodegrade at a controlled rate such that fine particles of the antagonist will be continuously released proximate to the biofilm. In some cases, the composites that can conform to the size and shape of the pockets can be fabricated using various methods, including 3D printing, to enhance contact between antagonist and biofilm thereby increasing treatment effectiveness as well as maximizing animal comfort.

In an embodiment, the inhibitor of the succinate/Sucnr1 signaling is provided as a topical formulation for use in the oral cavity. For example, compound 4C, 7a and/or 7b can be provided in the form of gel or strip formulations and applied topically onto the subgingival area by brushing daily (for gel formulation) or by inserting (for thin strip formulation). Treatment can be carried out for the any length of time as needed, such as over a period of days, weeks or months or longer and can be done as frequently as desired. For example, it can be done daily, or weekly or more or less frequently.

In an embodiment, the dosage of a compound of the present disclosure can be from 1.0 mg/kg to 500 mg/kg. For example, compound 4C can be used from 10 mg/kg to 100 mg/kg. For example, the dosage can be 10, 20, 30, 40, 50, 60, 70, 80, 90 and 100 mg/kg. In an embodiment, the dose is 50 mg/kg per application. Other compounds described herein, including 7a and 7b, can be used at similar dosages.

The oral films or other formulations may additionally comprise one or more of the following optional components: taste modifiers, bioadhesive agents, buffering agents, coloring agents, stabilizers, inert fillers, emulsifiers, pH adjusting agents, plasticizers, preservatives, and any other agent useful for release or stability of the active agent(s).

Suitable taste modifiers include flavorants, sweeteners, and taste-masking agents. Examples of taste modifying agents include, but are not limited to, the essential oils or water soluble extracts of menthol, wintergreen, peppermint, sweet mint, spearmint, vanilla, cherry, butterscotch, chocolate, cinnamon, clove, lemon, orange, raspberry, rose, spice, violet, herbal, fruit, strawberry, grape, pineapple, peach, kiwi, *papaya*, mango, coconut, apple, coffee, plum, watermelon, nuts, green tea, grapefruit, banana, butter and the like. Sweeteners (including artificial sweeteners) include sugar, honey, dextrose, lactose, aspartame, saccharin, sodium cyclamate, and acesulfame K.

Suitable colorants include, but are not limited to, pigments, dyes, natural food colors that are suitable for food and drug applications, such as any colorants approved by the FDA for food products and oral composition products, including dental products.

The oral film compositions and other oral compositions (e.g., chips) can comprise chelating agents, which can act as stabilizers. A common chelating agent is ethylenediaminetetraacetic acid (EDTA), however, any other biocompatible chelating agent can be used.

The oral film compositions or other oral formulations may also comprise inert fillers such as mannitol, xylitol, glucose, fructose, sucrose, sucralose, lactose, trehalose, maltodextrin, dextran, dextrin, modified starches, dextrose, sorbitol, dextrates, and mixtures thereof.

Suitable emulsifiers for oral compositions including films include castor oil derivatives, cetyl alcohol, ethanol, hydrogenated vegetable oils, polyvinyl alcohol, simethicone, sorbitan ester, glyceryl monostearate, polyoxyethylene alkyl ethers, polyoxyethylene stearates, poloxamer, polysorbates, and mixtures thereof. Other suitable additives include plasticizers, such as, alkylene glycols, polyalkylene glycols, glycerol, triacetin, deacetylated monoglyceride, diethyl salate, triethyl citrate, dibutyl sebacate, polyethylene glycols, and the like, and mixtures thereof.

The oral film composition or other oral formulations may also include one or more preservatives, such as, butylated hydroxyanisole (BHA), butylate hydroxytoluene (BHT), ascorbic acid, tocopherol derivatives, citric acid, parabens, derivatives of parabens, sorbic acid, salts of sorbic acid, sodium benzoate, propionic acid, salts of propionic acid, acetic acid, salts of acetic acid and the like.

The oral films can generally be prepared by dissolving the active agent in a suitable solvent, and mixing together with a film forming polymer, a compatible solvent, and optionally any one or more of the optional additives to form a mixture, which may be homogenous. A film can then be formed. Typically, a homogenous mixture of film components can be degassed and uniformly coated onto a casting substrate or extruded. The thickness can be adjusted as desired. The film can be made into desired shapes and sizes. As an example, the compounds of the present disclosure (such as 4C, 7a and/or 7b) may be used at a concentration of from 5 to 50 µM (e.g. 10 to 30 µM, such as 20 µM) using gelatin or chitosan using casting or dispersion methods.

Similarly, other formulations, such as tooth pastes, gels, oral rinses and the like can also be prepared by mixing the active agent with other components of the formulation. The viscosity of the in situ gel formulations can be from 2200 to 3200 cps. For example, in an embodiment, the viscosity of an in situ gel formulation measured at 37° C. was found to be 2304-3030.53±1.92 cps. Upon placement into the periodontal pockets or on gums, it is in contact with physiological pH and temperature 37° C. resulting in the formation of stiff gel with high strength and mucoadhesion properties. In an embodiment, the gels can have Poloxamer 407 (5-20% w/v) and Carbopol 934P (5-25%) formulated using 0.05-1:50 (W/V ratio) concentration of 4C.

Some examples of embodiments of the present disclosure are provided below.

An oral thin film having a thickness in the range of from 0.05 to 0.4 mm comprising an inhibitor of the succinate/succinate receptor 1 signaling pathway in the oral cavity, and a polymer. The succinate/succinate receptor 1 inhibitor in the oral thin film may be compounds 4C, succinate salt thereof, 7a, 7b, or a combination thereof. The polymer or the oral thin film may be an alginate, such as calcium alginate, or the polymer may be gelatin or chitosan or cellulose based polymer. In an embodiment, the succinate/succinate receptor 1 inhibitor in the oral thin film is compounds 4C, succinate salt thereof, 7a, 7b, or a combination thereof, and the polymer is calcium alginate. The succinate/succinate receptor 1 inhibitor and the calcium alginate may be present at a ratio (w/w) of 0.1 to 100 to 1:100. The oral thin film, when placed into the periodontal pockets or on gums, and upon the formulation coming in contact with physiological pH and temperature around 37° C. results in the formation of stiff strip/film with high strength and mucoadhesion properties.

A method of treating periodontal disease in an individual (human or non-human animal) comprising administering to the individual in need of treatment an oral film into the oral cavity of said individual, wherein the oral film has a thickness in the range of from 0.05 to 0.4 mm and comprises an inhibitor of the succinate/succinate receptor 1 signaling pathway (such as compounds 4C, 7a, 7b) in the oral cavity, and a polymer (such as alginate or other polymers disclosed herein).

The method of the present disclosure may be used on individuals afflicted with type 2 diabetes. The method can also be used in veterinary applications, including for pets such as dogs and cats.

The invention is further described through the following example, which is intended to be illustrative, and not restrictive.

Example 1

This example describes the preparation of two formulations for oral films.

In one formulation, calcium alginate strips were prepared as follows. A bubble-free suspension of 4C (dissolved in DMSO and purified) in sodium alginate solution was prepared in a ratio of 1:50 (w/w, drug:polymer). The suspension was added slowly dropwise into 0.1 mM $CaCl_2$) solution at room temperature using micro pipette. The beads were pressed wing titanium plates into thin films and let it dried at room temperature and stored at cold condition. The strips were tested using animal model of periodontal disease. Results of these studies are described in Example 2 below.

In another formulation, biodegradable polymers were used. (Nanoparticles, polyhydroxyalkanoates). These biopolymers are biocompatible and hydrophobic; they can also be turned into films, porous matrices, microcapsules, microspheres, and nanoparticles. Microparticles loaded with 4C (1:50 (w/w) drug:polymer) were prepared using the solvent evaporation technique. Aqueous phase as a dispersion medium for the microparticles production was prepared by using 0.5% (w/v) Poly Alcohol aqueous solution. The emulsion was agitated at 20,000 rpm with high performance homogenizer until the solvent had completely evaporated. Microparticles were collected by high speed centrifugation, rinsed in distilled water, and freeze dried and stored in cool and dry conditions.

Example 2

This example provides data which forms a basis for targeting SucnR1 to block osteoclastogenesis and periodontal bone loss in periodontitis.

We found that levels of succinate in GCF were greater in the patients with periodontitis and T2D (FIG. 1). We next investigated if selectively blocking the activity of SucnR1 in pre-osteoclasts could alleviate bone loss in diabetic mice. We synthesized a compound 4C which is a specific antagonist of the receptor SucnR1 and demonstrate herein its efficacy in blocking succinate stimulated osteoclastogenesis.

Figure 2:
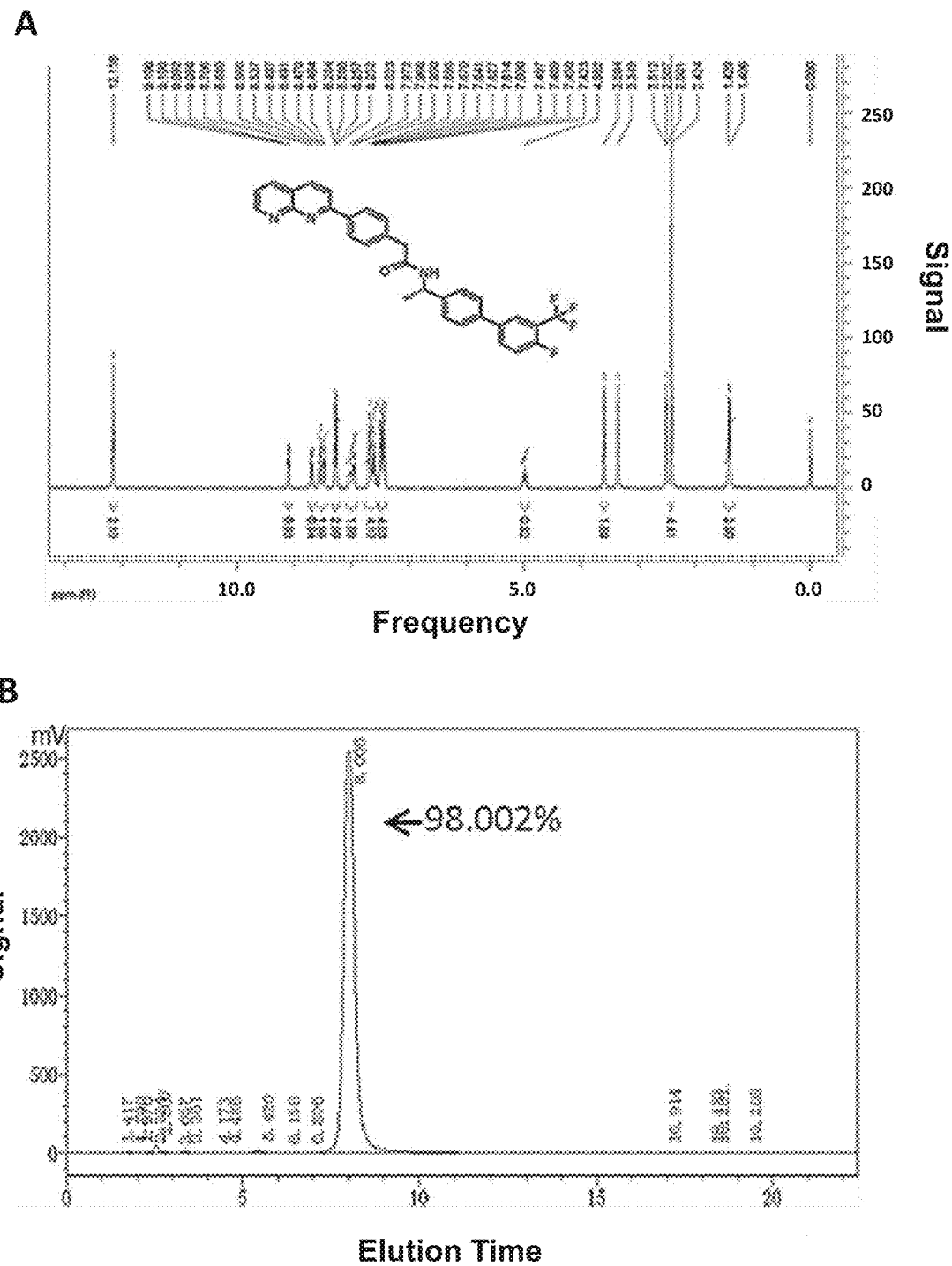
FIG. 2 shows succinate stimulates osteoclastogenesis via SUCNR1. (A) "4C" structure with NMR in dimethyl sulfoxide (DMSO). (B) Purity by high-performance liquid chromatography (HPLC). Ficoll processed non-adherent bone marrow cells were seeded at 20,000 per well in 96-well-plate and stimulated with the indicated concentration of cytokines (macrophage-colony stimulating factor (M-CSF), 30 ng ml$^{-1}$ from day 1; receptor activator of nuclear factor kappa-B ligand (RANKL), 50 ng ml$^{-1}$ from day 3); fresh cytokines were added every other day. (C) No cytotoxicity of 4C to the proliferation of osteoclast (OC) progenitors (without RANKL and M-CSF). (D-E) Representative TRAP staining images and analysis of WT mouse bone marrow in vitro OC cultures treated with 1 mM succinate or control in the presence of SucnR1 antagonist 4C at indicated concentrations. $p<0.01$, * $p<0.001$ according to Bonferroni post hoc test after ANOVA, N=5.
Figure 2:
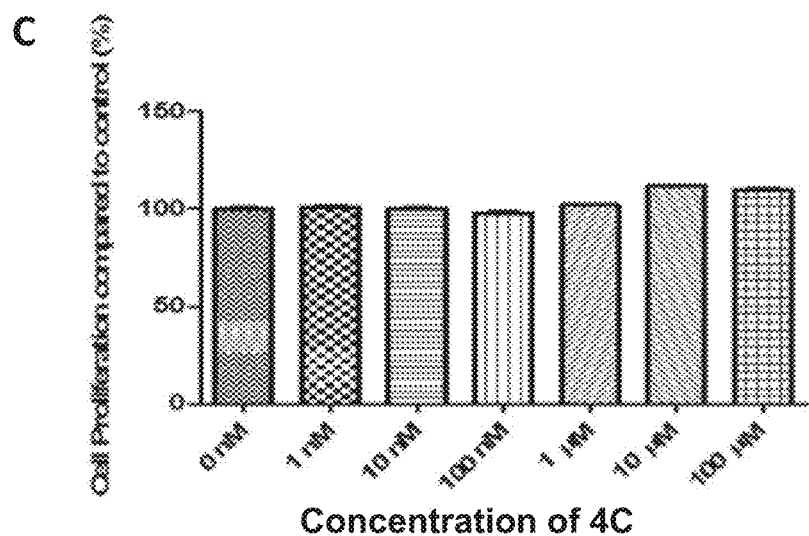
Figure 2:
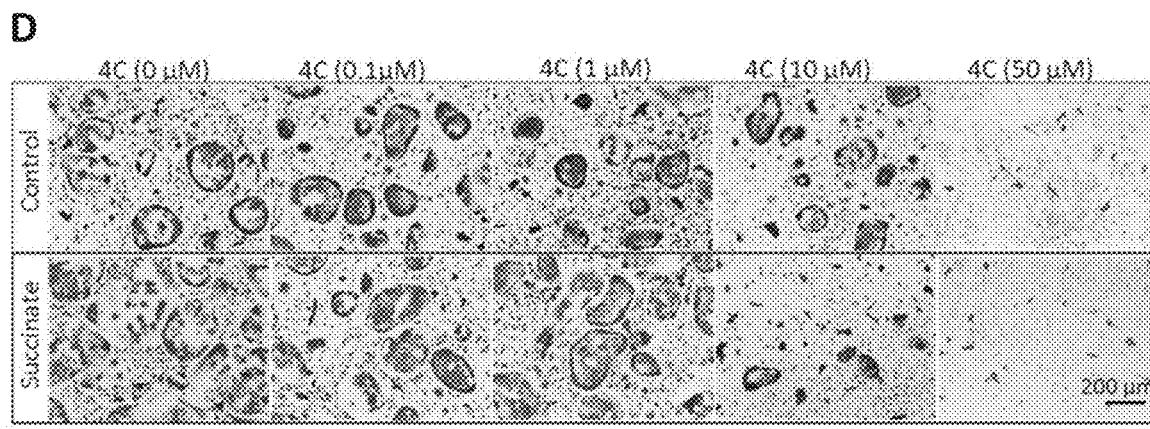
Figure 2:
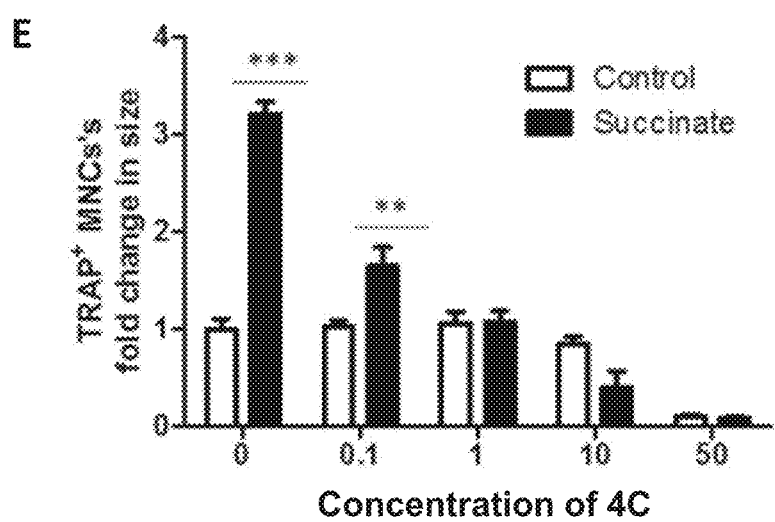

The structure of the synthetic antagonist of SucnR1 4C was authenticated using nuclear magnetic resonance spectroscopy (FIG. 2A) with a purity of 98.002% according to high-performance liquid chromatography (FIG. 2B). At up to 100 μM, 4C has no inhibitory effect on the viability of pre-osteoclastic cells (FIG. 2C) which indicates it has none or very low cytotoxicity. The impact of 4C at 0.1 μM, 1 μM, 10 μM and 50 μM in the osteoclast culture derived from ficoll processed mouse bone marrow cells were tested and 4C started to reduce the stimulation of succinate at 0.1 μM. At 10 μM it was able to completely erase the simulation of osteoclastogenesis by succinate in vitro (FIG. 2D-E).

Figure 3:
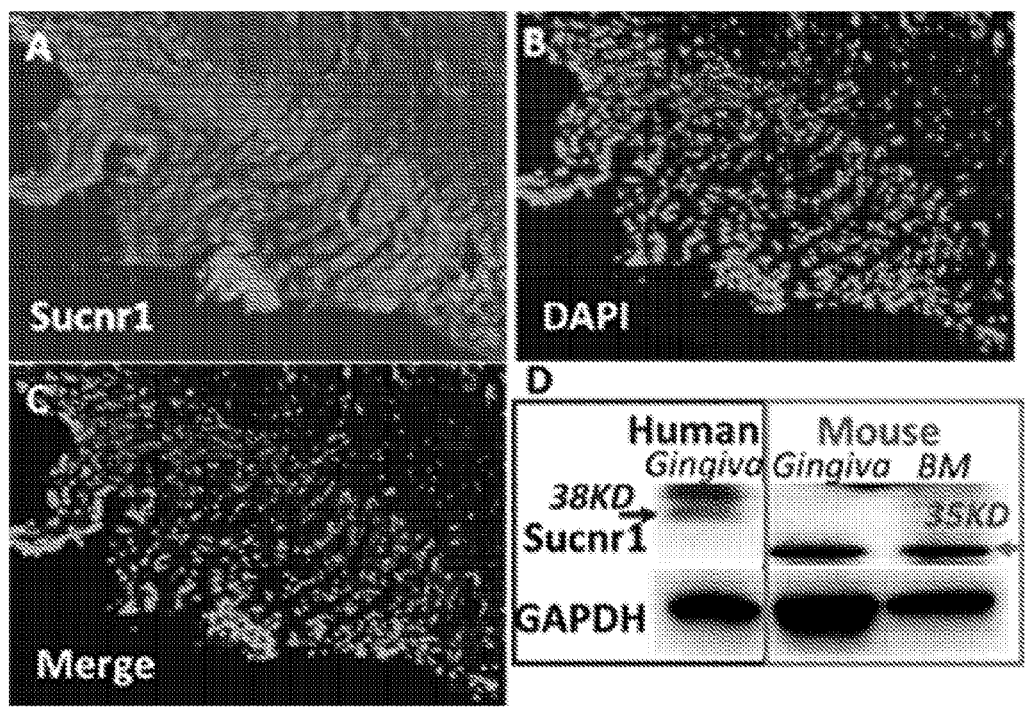
FIG. 3 shows SucnR1 expression. A-C Sections of gingiva from patient with periodontitis were treated for antigen retrieval and rehydration, and incubated with SucnR1 antibody overnight at 4° C. SucnR1 antibody was localized with biotinylated secondary antibody and Alexa 594 conjugated 2$^{nd}$ antibody then mounted with DAPI-containing mounting medium. D. Western blotting images of SucnR1 and glyceraldehyde-3-phosphate dehydrogenase (GAPDH) in non-diabetic human and mouse gingiva. Bone marrow (BM) protein was used as a positive control.
Figure 4:
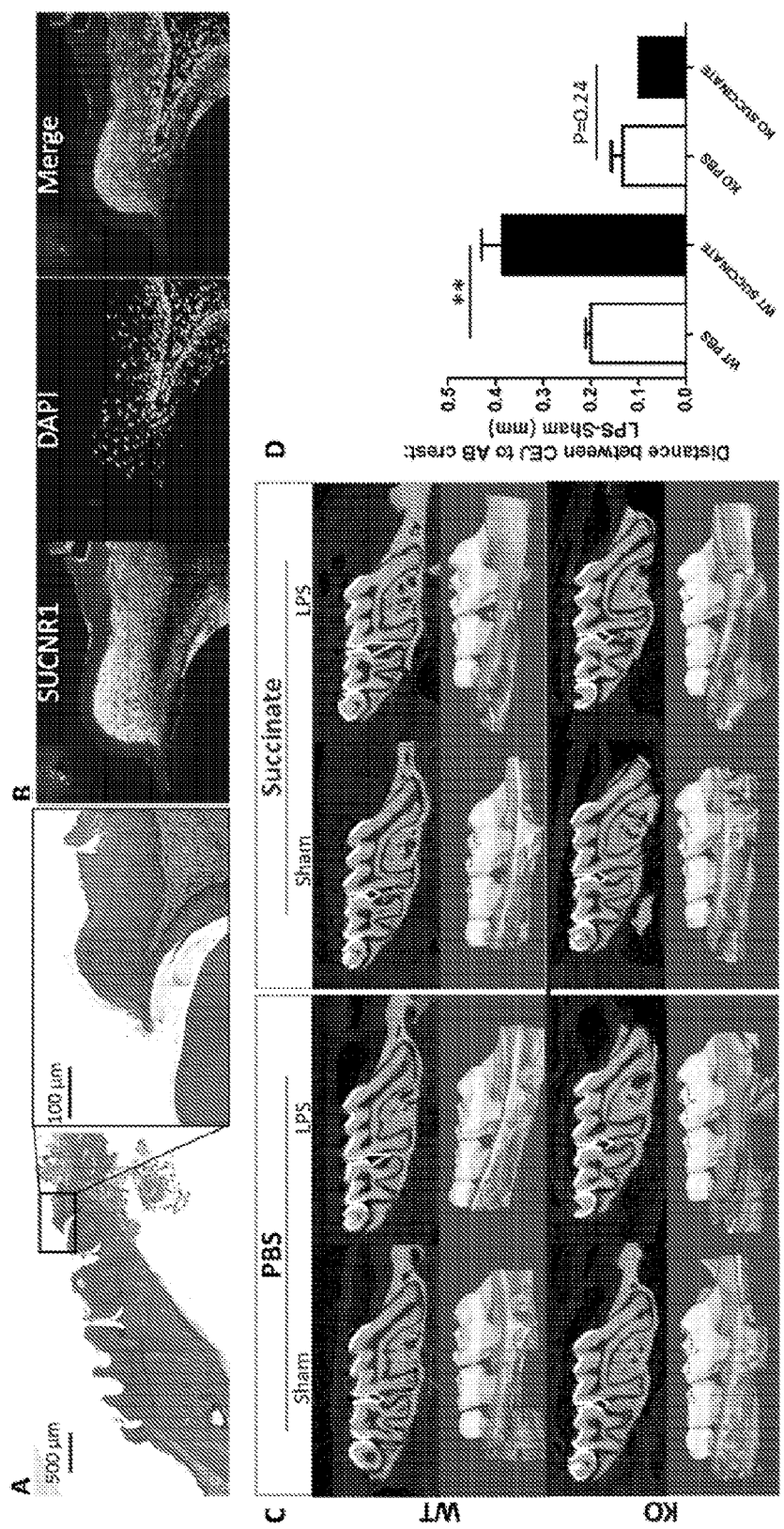
FIG. 4. Sucnr1 deficient mice are protected from LPS-induced periodontal bone loss. (A) Representative hematoxylin and eosin (H&E) staining images of the mice maxillae, and (B) immunofluorescence staining of sucnR1. (C) Representative microCT images of the maxillae. Maxillae sagittal plane images (background images) with lines to indicate the distance between CEJ to AB crest, and 3D images of the certain side of the maxillae (background images). (D) Quantification of distance between CEJ to AB crest (subtract distance of sham side from LPS side in each mice) in mm (n=6, two tailed t test, ** $p<0.005$).

Expression of the succinate receptor SucnR1 was found in both human and mouse gingival tissues (FIG. 3). Particularly, SucnR1 protein is highly expressed in the stratified squamous cells as indicated by the intensive green florescent colored cell layers along the gingiva tissue between teeth in mice (FIG. 4A-B). To determine whether succinate signaling mediated through SucnR1 plays a critical role in accelerating LPS-induced periodontal bone loss, alveolar bone loss in WT and SucnR1 KO mice receiving PBS or succinate treatment were compared using the LPS injection periodontal disease model (FIG. 4C-D). Succinate enhanced periodontal bone loss in WT mice but not in KO mice. The distances between the alveolar bone crest to the cementoenamel junction (CEJ) were compared to indicate the degree of bone loss among different groups. In WT mice, the difference in the distance between CEJ to alveolar bone crest at the LPS injected side and sham injected side was enhanced by systemic succinate administration at close to two-fold in WT mice. In contrast, in KO mice, the administration of succinate did not further enhance bone loss induced by LPS injection. Furthermore, comparisons between WT and KO mice treated with PBS show that absence of Sucnr1 protects alveolar bone loss induced by LPS. This result indicates that activation of SucnR1 contributes to LPS-induced bone loss in mice.

Figure 5:
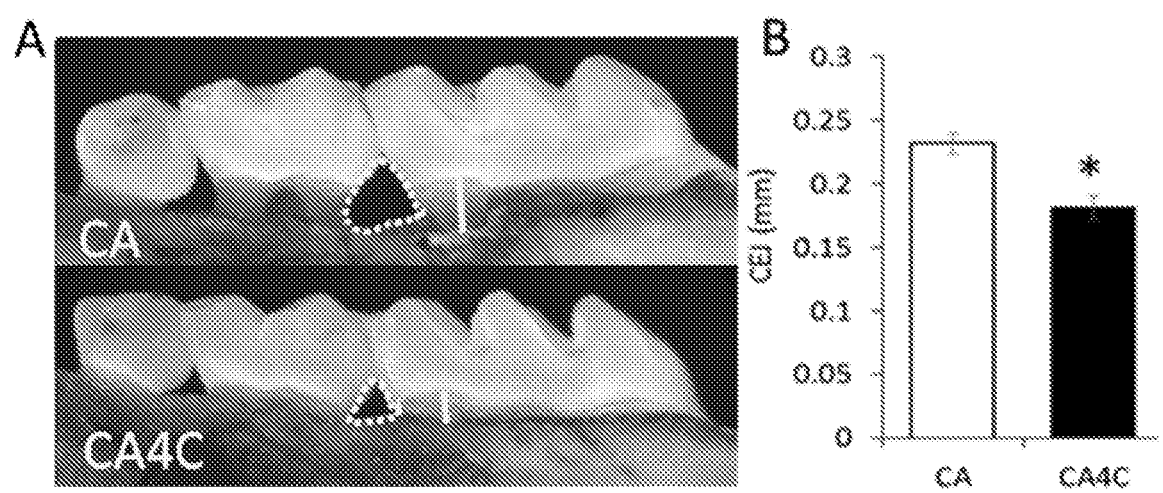
FIG. 5 shows P. gingivalis derived LPS (InvivoGen, San Diego, Calif.) were injected between the 1st and 2nd maxillary molar on the left side treatment (3 times/week). All mice received daily injection of succinate to mimic the elevation of succinate in diabetic mice. Mice were randomly assigned to CA or CA4C group. BP and BP4C were applied between the gingival tissue and tooth root at the same time when LPS was injected. The dosage of 4C was 50 mg/kg per application. A. Representative images of the maxillary molars. B. The distances between the alveolar bone crest to the cementoenamel junction indicating the degree of bone loss were quantitated. (Mean±SEM, N=3, *$p<0.05$).

Further, we made Calcium alginate (CA) strips with and without 4C and tested the strips in mouse periodontitis model. (Hiyari, S., et al., Heritability of periodontal bone loss in mice. J Periodontal Res, 2015. 50(6): p. 730-6). Results indicates that CA with 4C (CA4C) effectively reduced periodontal bone loss and root exposure induced by *P. gingivalis* lipopolysaccharide (LPS) (FIG. 5).

Briefly, the experiments were conducted as described below: Mice were anesthetized with 2-5% isoflurane through a nose cone. Thrice weekly, using a 10-μl Hamilton syringe with a 33 gauge needle, 10 μg *Porphyromonas gingivalis*-derived LPSs (InvivoGen, San Diego, Calif.) in 2 μl sterile endotoxin free water (InvivoGen, San Diego, Calif.) were injected into the gingival tissue between the right 1st and 2nd maxillary molars. At the same point on the left side and using a same-sized needle, 2 μl sterile endotoxin free water was injected as a sham treatment. Mice were randomly assigned to CA or CA4C group. CA or CA4C were applied between the gingival tissue and tooth root at the same time when LPS was injected for 4 weeks. Mice were monitored daily to provide oral hygiene and assess healing and inflammation before being euthanized after 4 weeks of treatment. Serum, periodontium tissue, maxilla, mandible, and long bones from hind limbs were collected for analysis.

Example 3

The following example further describes synthesis and uses of compounds and films of the present disclosure.

Scheme 1 shows a synthetic route of Compound 7a and 7b.

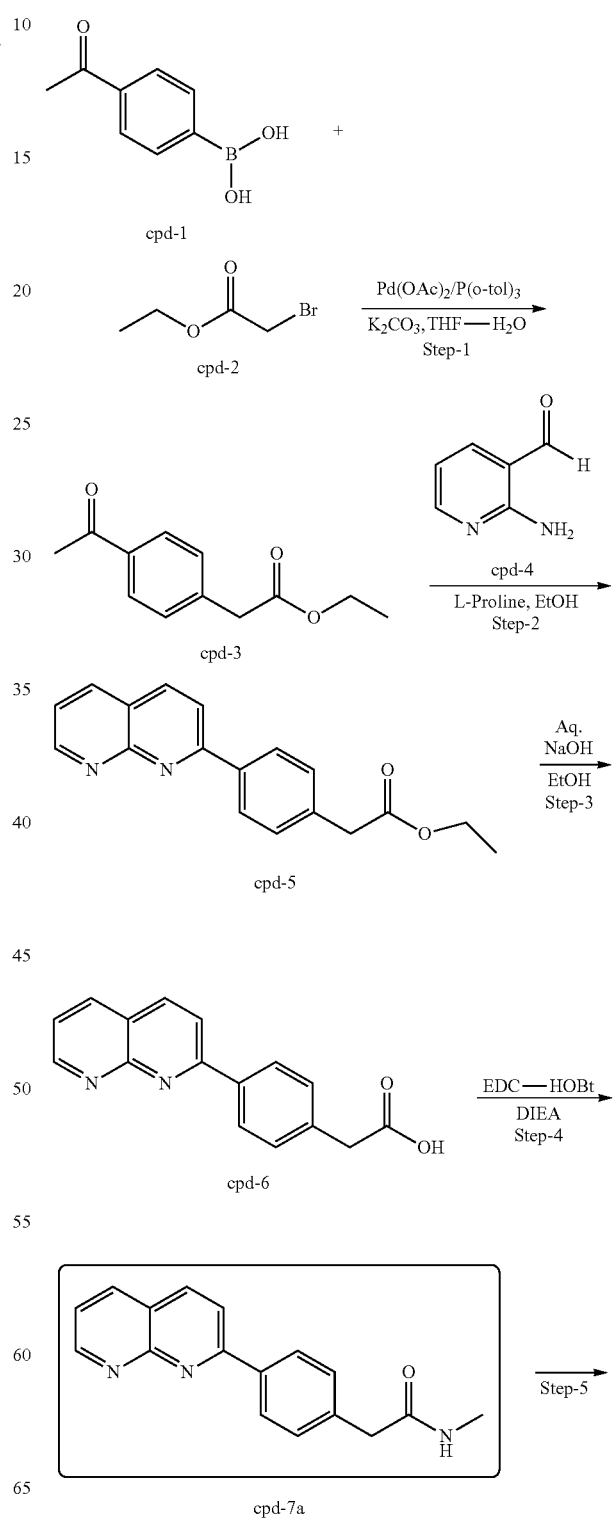

-continued

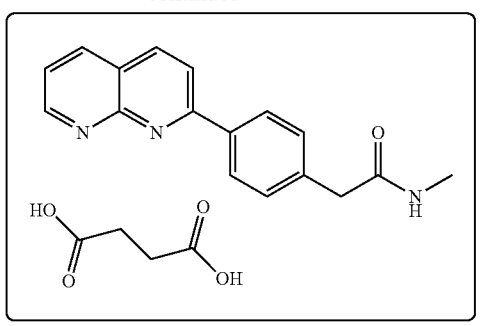

cpd-7b

-continued

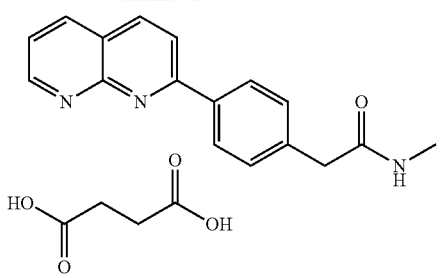

CF: C₂₁H₂₁N₃O
MW: 395
cpd-7b

Scheme 1 correlates to the following steps:

| Step | Reaction scale/conditions | Results |
|---|---|---|
| 1 | cpd-1 (3.34 g, 1 eq.), cpd-2 (3.93 g, 1.2 eq).), Pd(OAc)₂ (3 mol %), P(o-tol)₃ (9 mol %), K₂CO₃(5 eq), THF, H₂O, rt, 16 h | Isolated cpd-3: 3.05 g (Y: 74%) Confirmed by 1HNMR analysis |
| 2 | cpd-3 (1.5 g, 1 eq.), cpd-4 (0.88 g, 1 eq.), L-proline (1.0 eq.), EtOH, reflux, 12 h | Isolated cpd-5: 1.1 g (Y: 52%) Confirmed by 1HNMR analysis |
| 3 | cpd-5 (1.0 g, 1 eq.), NaOH (3.0 eq), EtOH, H₂O, rt, 3 h | Isolated cpd-6: 0.8 g (Y: 88%) Confirmed by 1HNMR analysis |
| 1 | cpd-1 (11.7 g, 1 eq.), cpd-2 (9.94 g, 1.2 eq).), Pd(OAc)₂ (3 mol %), P(o-tol)₃ (9 mol %), K₂CO₃ (5 eq), THF, H₂O, rt, 16h. | Isolated cpd-3: 9.5 g (Y: 77%) Confirmed by 1HNMR analysis |
| 2 | cpd-3 (6.0 g, 1 eq.), cpd-4 (3.55 g, 1 eq.), L-proline (1.0 eq.), EtOH, reflux, 12 h | Purification under progress. Compound was purified by column chromatography on silica gel, followed by second purification with ether trituration. Isolated cpd-5: 3.1 g (Y: 37%) Confirmed by 1HNMR analysis |
| 3 | cpd-5 (2.5 g, 1 eq.), NaOH (1.1 eq), EtOH, H₂O, rt, 3 h | Purified by trituration with ether Isolated cpd-6: 1.0 g (Y: 44.2%) Confirmed by 1HNMR analysis Yield was little low, probably lost some acid in the aqueous layer. |

Scheme 2 also shows a synthetic route for compounds 7a and 7b.

Scheme 2 correlates to the following steps:

| Step | Reaction scale/conditions | Results |
|---|---|---|
| 3a | cpd-5 (0.3 g, 1 eg.), MeNH₂ (2M in THF, 5.5 mL, 10 eq.), DBU (0.2 eq.), rt, 3 days. | Crude compound was purified by trituration with Ether. Isolated cpd-7a free base: 0.28 g (Y: quant.). Confirmed by 1HNMR and 13C NMR and LCMS analyses. |
| 3a | cpd-5 (1.5 g, 1 eq.), MeNH₂ (2M in THF, 12.8 mL, 5 eq.), DBU (0.2 eq.), rt, 3 days. | Crude compound was purified by trituration with Ether. Isolated cpd-7a free base: 1.1 g (Y: 77%). Confirmed by 1HNMR and 13C NMR and LCMS analyses. HPLC purity: >98% |
| 3a | cpd-5 (1.6 g, 1 eq.), MeNH₂ (2M in THF, 12.8 mL, 5 eq.), DBU (0.2 eq.), rt, 3 days. | Crude compound was purified by trituration with Ether followed by EtOAc. Isolated cpd-7a free base: 1.28 g (Y: 84.4%). Confirmed by 1HNMR and 13C NMR and LCMS analyses. |
| 5 | cpd-7a (1.0 g, 1 eq.), Succinic acid (0.22 g, 0.5 eq.), Acetone (10 mL), 60° C., 16 h. | Crude compound was purified by trituration DCM. Isolated cpd-7b: 0.8 g (56.2%) Compound was confirmed by 1HNMR spectroscopy. |

Scheme 3 shows a synthetic route for an intermediate of 4C.

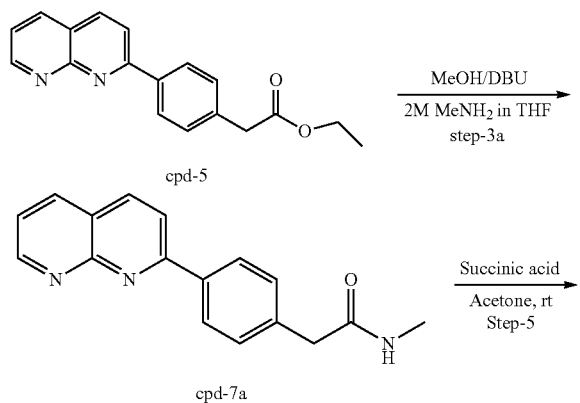

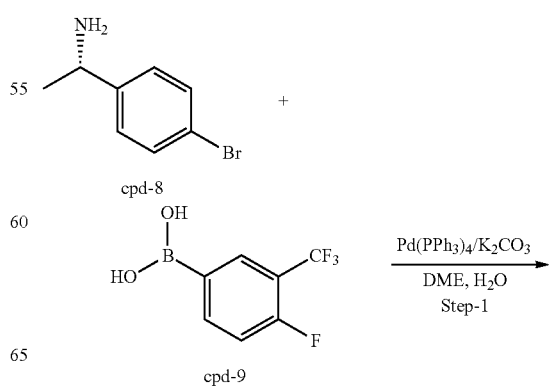

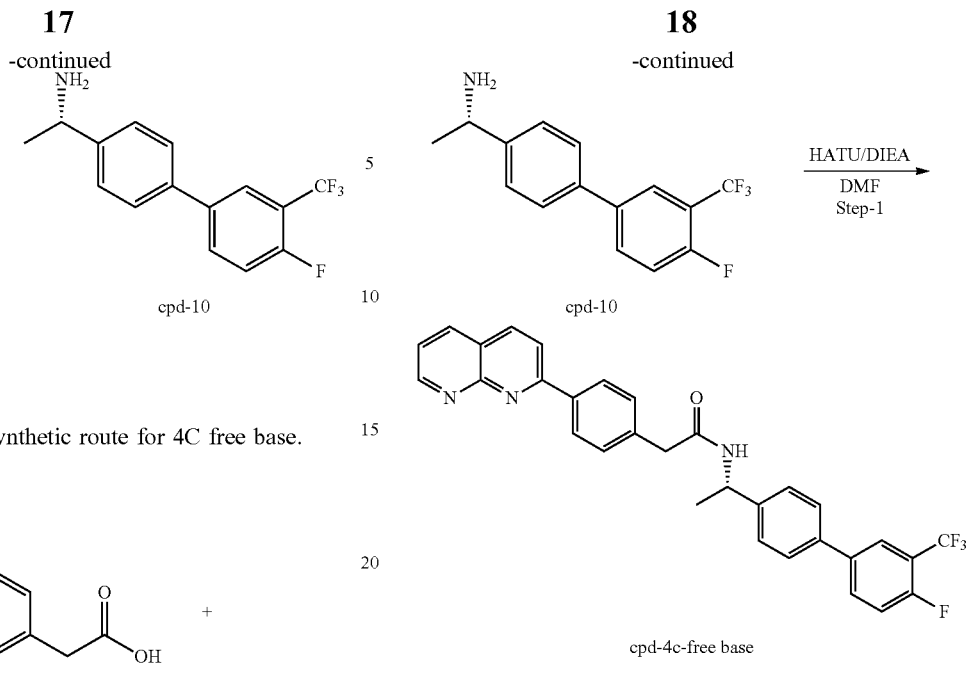
Scheme 4 shows a synthetic route for 4C free base.
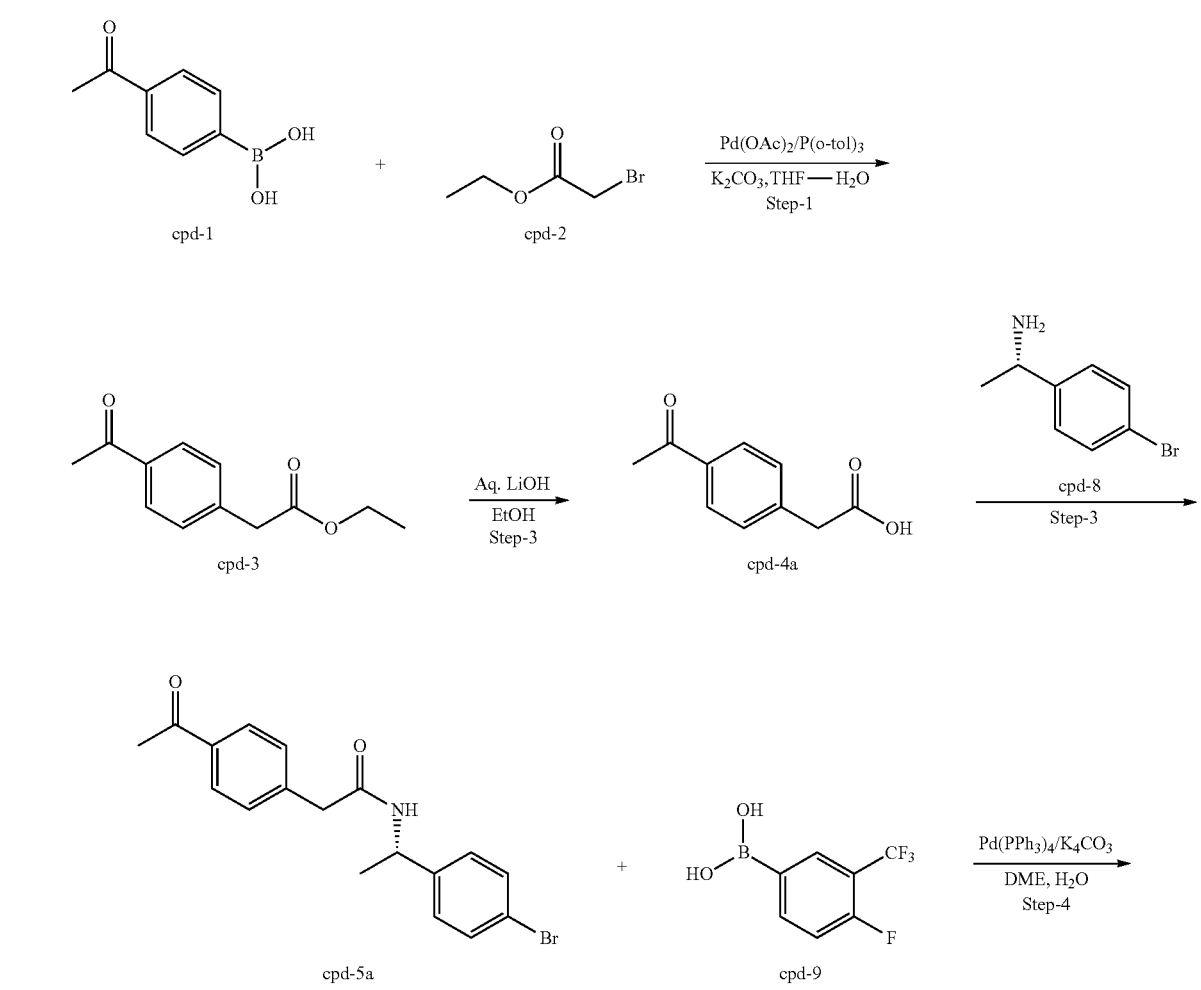
Scheme 5 shows an alternative synthetic route for 4C free base.

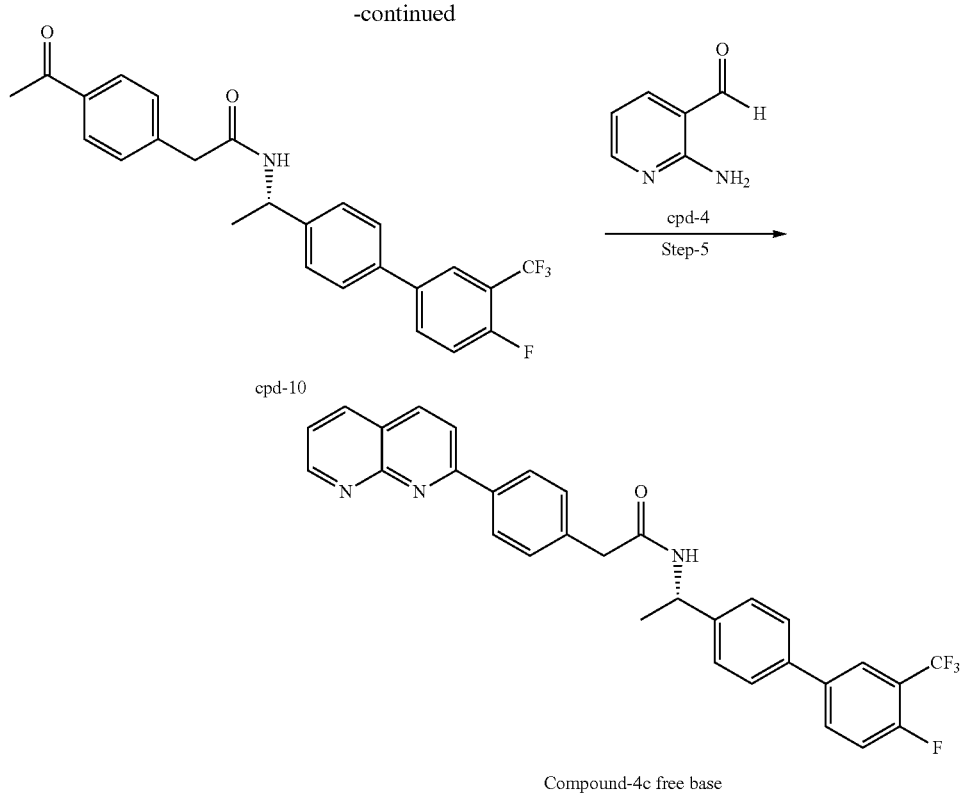

Scheme 5 correlates to the following steps:

| Step | Reaction scale/conditions | Results |
|---|---|---|
| 2 | cpd-3 (1.0 g, 1 eq.), LiOH · H₂O (0.61 g, 3.0 eq), H₂O (3 mL), EtOH, rt, 3 h | Isolated cpd-4a: 0.7 g (Y: 94%) Confirmed by 1HNMR analysis |
| 3 | cpd-4a (0.8 g, 1 eq.), cpd-8 (0.7 mL, 1.1 eq.), EDC · HCl (1.29 g, 1.5 eq.), DIEA (1.6 mL, 1.0 eq.), DCM, rt, 16 h | Isolated cpd-5: 0.3 g (Y: 19%) Confirmed by 1HNMR analysis |
| 4 | cpd-5a (0.25 g, 1 eq.), cpd-9 (0.29 g, 2.0 eq.), Pd (PPh₃)₄ (5 mol %), K₂CO₃ (1.5 eq.), ACN, 80° C., 16 h | Crude was purified by column chromatography on silica gel Isolated cpd-10: 0.21 g (Y: 69%) Confirmed by 1HNMR analysis |
| 5 | cpd-10 (0.2 g, 1 eq.), cpd-4, (55.1 mg 1 eq.), L-proline (1.0 eq.), EtOH, reflux, 24 h. | Isolated cpd-4C free base: 0.2 g (Y: 84%) Confirmed by 1HNMR analysis |

Example 4

Figure 8:
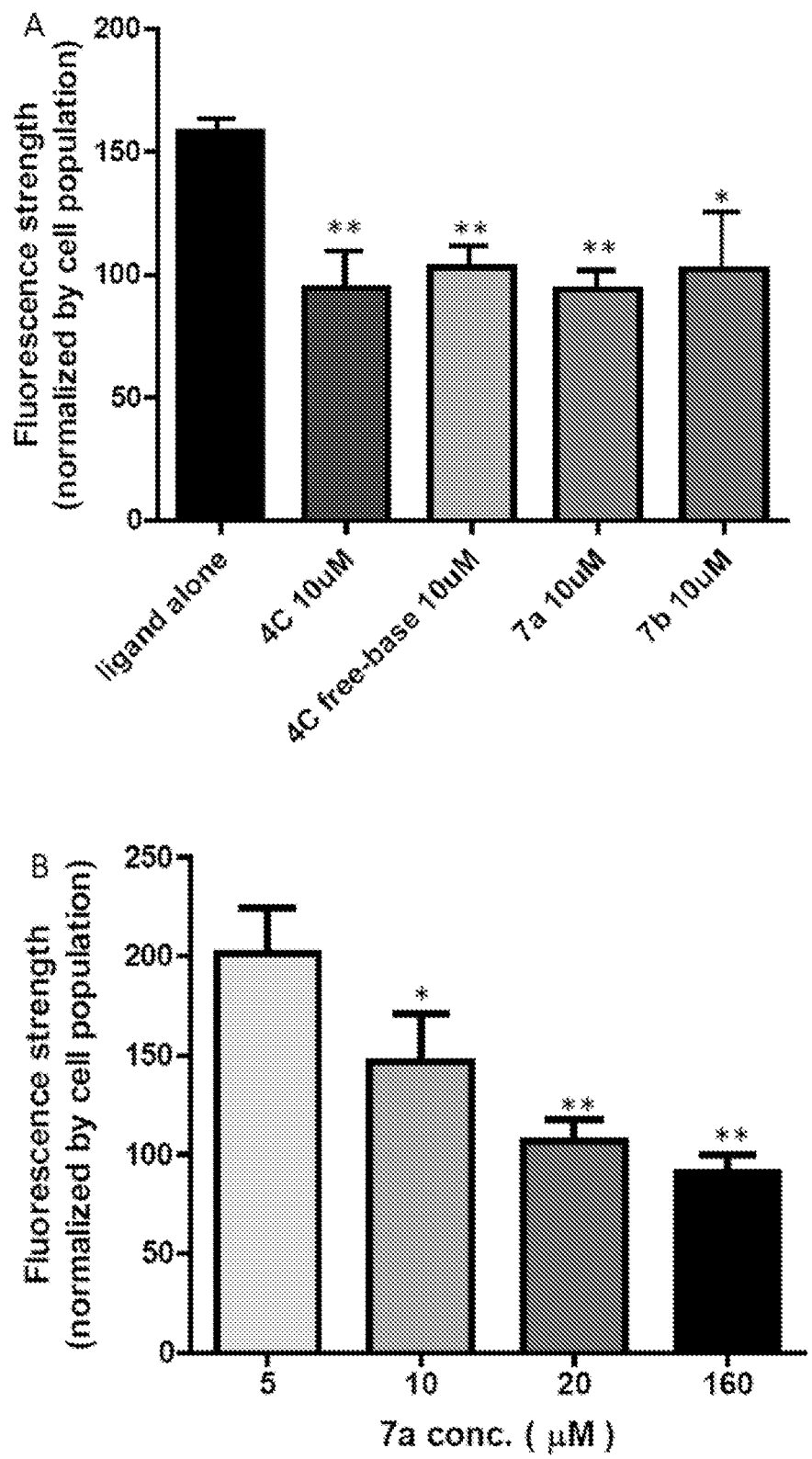
FIG. 8 shows the efficacy of several SUCNR1 antagonists in suppression the activity of SUCNR1. Human Succinate Receptor 1 AequoScreen® Cell Line (PerkinElmer ES-744-A) was used to assess the activity of SUCNR1 upon activation by ligand (succinate 500 μM) in the presence and absence of antagonists. Cells were seeded at 5,000 cells/well for 24 hour before the calcium dye was added. Forty-five minutes later, the antagonists were added at indicated concentrations. Fifteen minutes later, the ligand was added and the fluorescent signal (EX/EM: 485/525) was measured immediately on a plate reader. A) The efficacy of 3 newly synthesized compounds in comparison with 4C at the same concentration. (*$p<0.05$, **$p<0.001$ by t-test in comparison to ligand alone post One-Way ANOVA) B) Dose effects of the compound 7a at various concentrations. (*$p<0.05$, **$p<0.001$ in comparison to 5 M by t-test post One-Way ANOVA).

Structure-activity relationship studies were performed using the compounds depicted in FIG. 7. The structure and purity of the compounds were confirmed via HPLC and NMR. At the same concentration of 4C, these antagonists inhibited the activation of SucnR1 by succinate in vitro (FIG. 8A). This result suggested that the antagonist in succinic acid salt form (4C and Cpd-7b) exhibit similar efficacy as their free base form. One of the antagonists, Cpd-7a was tested with different concentrations and demonstrated 50% inhibition at 20 µM (FIG. 8B). These data are depicted in FIG. 8.

While the present invention has been described through specific examples, routine modifications to the disclosure will be apparent to those skilled in the art. Such modifications are intended to be within the scope of the disclosure.

What is claimed is:

1. An oral thin film having a thickness of from 0.05 mm to 0.4 mm comprising an inhibitor of the succinate/succinate receptor 1 signaling pathway in the oral cavity, and a polymer, wherein the inhibitor of succinate/succinate receptor has the following structure or a succinate salt thereof:

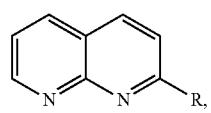

where R is selected from the group consisting of a hydrogen atom, an alkyl group, COOR' group, and

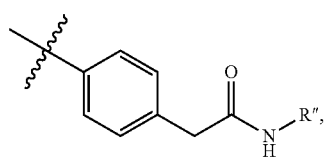

where R' is an alkyl group and R" is selected from the group consisting of a hydrogen atom, an alkyl group, and

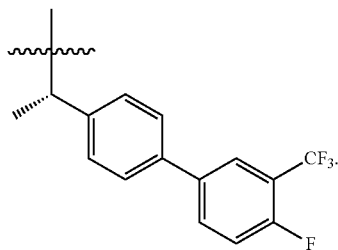 [SMILES: *[C@@H](C)c1ccc(-c2ccc(F)c(C(F)(F)F)c2)cc1]

2. The oral thin film of claim 1, wherein the succinate/succinate receptor 1 inhibitor has the following structure:

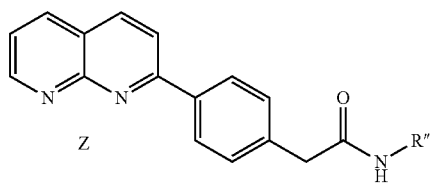

where R" is selected from the group consisting of a hydrogen atom, an alkyl group, and

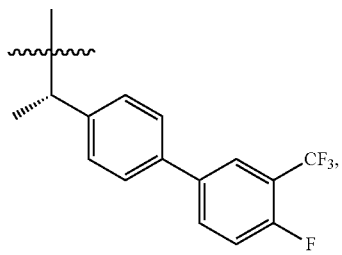 [SMILES: *[C@@H](C)c1ccc(-c2ccc(F)c(C(F)(F)F)c2)cc1]

and where Z is optional and when present, is a succinate group.

3. The oral thin film of claim 1, wherein the succinate/succinate receptor 1 inhibitor is selected from the group consisting of

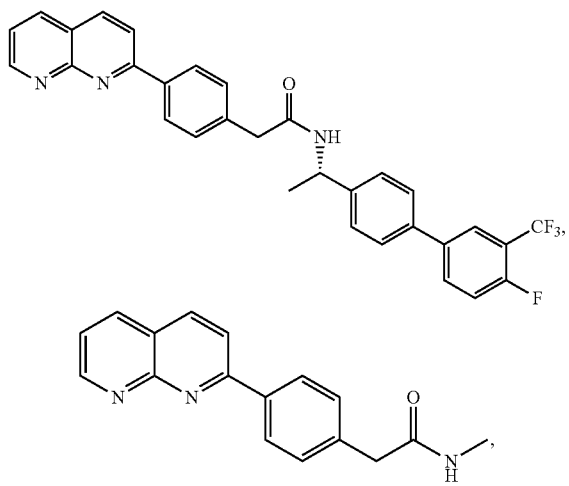

and succinate salts thereof.

4. The oral thin film of claim 1, wherein the polymer is an alginate.

5. The oral thin film of claim 4, wherein the alginate is a calcium alginate.

6. The oral thin film of claim 1, wherein the polymer is a gelatin, a chitosan, or a cellulose based polymer.

7. The oral thin film of claim 1, wherein the succinate/succinate receptor 1 inhibitor is selected from the group consisting of

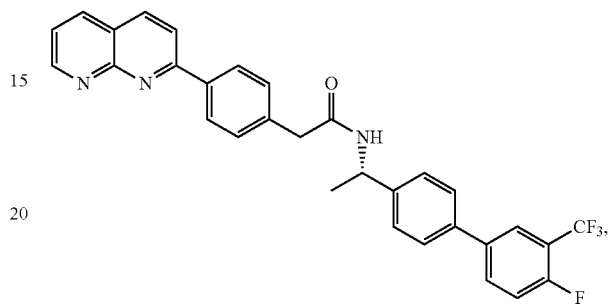

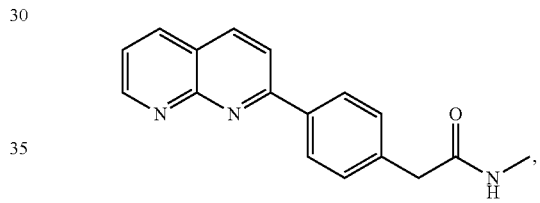

and succinate salts thereof, and the polymer is a calcium alginate.

8. The oral thin film of claim 7, wherein the succinate/succinate receptor 1 inhibitor and the calcium alginate are present in a ratio (w/w) of 1:10 to 1:100.

9. The oral thin film of claim 8, wherein the succinate/succinate receptor 1 inhibitor and the calcium alginate are present at the ratio (w/w) of 1:50.

10. A method of treating periodontal disease in an individual in need thereof, the method comprising administering to the oral cavity of the individual the oral film of claim 1.

11. The method of claim 10, wherein the succinate/succinate receptor 1 inhibitor in the oral film has the following structure:

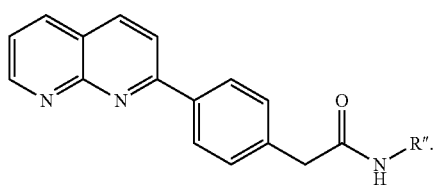

12. The method of claim 10, wherein the succinate/succinate receptor 1 inhibitor in the oral film is selected from the group consisting of

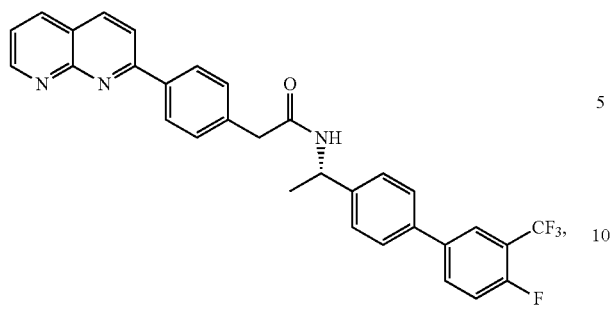
succinate salts thereof, and combinations thereof.
13. The method of claim 10, wherein the individual is afflicted with type 2 diabetes.
14. The method of claim 10, wherein the individual is a human.
15. The method of claim 10, wherein the individual is a non-human animal.
16. The method of claim 15, wherein the non-human animal is a cat or a dog.
* * * * *

UNITED STATES PATENT AND TRADEMARK OFFICE
CERTIFICATE OF CORRECTION

Page 1 of 1

PATENT NO. : 11,376,216 B2
APPLICATION NO. : 16/959614
DATED : July 5, 2022
INVENTOR(S) : Xin Li and Deepak Saxena It is certified that error appears in the above-identified patent and that said Letters Patent is hereby corrected as shown below:

In the Specification

Column 1, Line 9 should read:
--STATEMENT REGARDING FEDERALLY SPONSORED RESEARCH OR DEVELOPMENT
This invention was made with government support under grant numbers R21 AG055787 and R01 DE027074 awarded by The National Institutes of Health. The government has certain rights in the invention.--

Signed and Sealed this
Sixth Day of December, 2022

Katherine Kelly Vidal
*Director of the United States Patent and Trademark Office*